(12) United States Patent
Cheng et al.

(10) Patent No.: US 7,240,042 B2
(45) Date of Patent: Jul. 3, 2007

(54) SYSTEM AND METHOD FOR BIOLOGICAL DATA ANALYSIS USING A BAYESIAN NETWORK COMBINED WITH A SUPPORT VECTOR MACHINE

(75) Inventors: Jie Cheng, Princeton, NJ (US); Chao Yuan, Plainsboro, NJ (US); Bernd Wachmann, Lawrenceville, NJ (US); Claus Neubauer, Monmouth Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 11 days.

(21) Appl. No.: 11/208,743

(22) Filed: Aug. 22, 2005

(65) Prior Publication Data

US 2006/0047616 A1    Mar. 2, 2006

Related U.S. Application Data

(60) Provisional application No. 60/604,233, filed on Aug. 25, 2004.

(51) Int. Cl.
*G06N 5/00* (2006.01)

(52) U.S. Cl. .............................. 706/52; 706/45; 706/48

(58) Field of Classification Search ................. 706/52, 706/48, 45, 47; 435/6; 702/20
See application file for complete search history.

(56) References Cited

U.S. PATENT DOCUMENTS 6,714,925 B1 *   3/2004   Barnhill et al. ............... 706/48

OTHER PUBLICATIONS

Cheng J et al, "An Algorithm for Bayesian Belief Network Construction From Data", Proceedings of the 6th International Workshop on Artificial Intelligence and Statistics, 1997, AI&STAT, 1997.
Casasent D et al, "Face Recognition with Pose and Illumination Variations Using New SVRDM Support-Vector Machine", Optical Engineering, vol. 43, No. 8, Aug. 2005, Society of Photo-Optical Instrumentation Engineers, pp. 1804-1813.

* cited by examiner

*Primary Examiner*—Wilbert L. Starks, Jr.
(74) *Attorney, Agent, or Firm*—Michele L. Conover (57) ABSTRACT

A method for analyzing biological data includes classifying a first set of biological data in a first classifier, classifying a second set of biological data in a second classifier, combining the results of the first classifier with the results of the second classifier, and analyzing the results as a function of the similarity measure of the first classifier and the similarity measure of the second classifier.

15 Claims, 4 Drawing Sheets

SYSTEM AND METHOD FOR BIOLOGICAL DATA ANALYSIS USING A BAYESIAN NETWORK COMBINED WITH A SUPPORT VECTOR MACHINE

CROSS REFERENCE TO RELATED UNITED STATES APPLICATIONS

This application claims priority from "A combination of Bayesian networks and an improved support vector machines for the analysis of biological data", U.S. Provisional Application No. 60/604,233 of Cheng, et al., filed Aug. 25, 2004, the contents of which are incorporated herein by reference.

TECHNICAL FIELD

This invention is directed to the analysis of biological data using learning tools such as Bayesian networks and support vector machines (SVMs).

DISCUSSION OF THE RELATED ART

One area of concern in bioinformatics is the discovery of dependencies e.g., in genetic networks based on microarray data and their change from a healthy state due to illness. These data have inherent noise for biological and technical reasons and require advanced technologies to extract useful information for the subsequent classification.

Two methods for extracting these dependencies are Bayesian networks and support vector machines. Bayesian networks (BN) are powerful tools for knowledge representation and inference under conditions of uncertainty. A Bayesian network $B=[N, A, \Theta]$ is a directed acyclic graph (DAG) where each node $n \in N$ represents a domain variable, and each edge $a \in A$ between nodes represents a probabilistic dependency, quantified using a conditional probability distribution $\theta_i \in \Theta$ for each node $n_i$. A Bayesian network (BN) can be used to compute the conditional probability of one node, given values assigned to the other nodes; hence, a BN can be used as a classifier that gives the posterior probability distribution of the node class given the values of other attributes. An advantage of BNs over other types of predictive models, such as neural networks, is that the Bayesian network structure represents the inter-relationships between the dataset attributes. Human experts can easily understand the network structures and if necessary modify them to obtain better predictive models.

Support vector machines (SVMs) are techniques that have been developed for statistical pattern recognition, and have been applied to many pattern recognition areas. SVMs are primarily two-class classifiers that have a margin between the two classes, and have training patterns called support vectors that define the classification function. SVMs have been proven to be powerful classification tools that exhibit good generalization. This can be attributed to the fact that the regulation term in an SVM not only overcomes the over-training problem, which typical neural networks have, but also maximizes the separation between classes. However, an SVM does not reject data that does not meet the classification criteria. Use of a decision threshold can make the SVM reject data, but such SVMs have poor rejection performance, because the SVM produces a large decision region for each class, leading to high false alarm rates.

SUMMARY OF THE INVENTION

Exemplary embodiments of the invention as described herein generally include methods and systems for combining a Bayesian network with an improved SVM for the analysis of biological data. A new support vector representation and discrimination machine has comparable discrimination performance as the SVM, but much better rejection performance, while a new BN learning algorithm is based on a three-phase dependency analysis, which is especially suitable for data mining in high dimensional data sets due to its efficiency. The performance of the SVMs was improved by addressing rejection-classification, where there are M object classes to be discriminated and one non-object class to be rejected. This non-object class could be anything except the M object classes.

According to an aspect of the invention, there is provided a method for analyzing biological data, the method including classifying a first set of biological data in a first classifier, classifying a second set of biological data in a second classifier, combining the results of the first classifier with the results of the second classifier, and analyzing the results as a function of the similarity measure of the first classifier and the similarity measure of the second classifier.

According to a further aspect of the invention, the first set of biological data and the second set of biological data are the same.

According to a further aspect of the invention, the first classifier is a support vector representation and discrimination machine.

According to a further aspect of the invention, the second classifier is a Bayesian network.

According to a further aspect of the invention, the first set of biological data is a set of microarray data.

According to a further aspect of the invention, the second set of biological data is a set of protein mass spectra.

According to a further aspect of the invention, the results of the first classifier and the second classifier are combined in parallel.

According to a further aspect of the invention, the Bayesian network comprises computing mutual information of pairs of data of said data set, creating a draft network based on the mutual information, wherein data item of said data set comprise nodes of said network and the edges connecting a pair of data nodes represent the mutual information of said nodes, thickening said network by adding edges when pairs of data nodes cannot be d-separated, and thinning said network by analyzing each edge of said draft network with a conditional independent test and removing said edge if said corresponding data nodes can be d-separated.

According to a further aspect of the invention, the combining step comprises weighing the results of the first and second classifiers based on the input patterns.

According to another aspect of the invention, there is provided a program storage device readable by a computer, tangibly embodying a program of instructions executable by the computer to perform the method steps for analyzing biological data.

DETAILED DESCRIPTION OF THE PREFERRED EMBODIMENTS

Exemplary embodiments of the invention as described herein generally include systems and methods for combining two classifiers for both analyzing the same type of data as well as analyzing data from different sources having different biomolecular information.

According to an embodiment of the invention, a first combination of a support vector representation and discrimination machine (SVRDM) and Bayesian network (BN) are utilized for analyzing the same set of micro array data. A second combination of the SVRDM and BN are utilized for analyzing the same set of protein mass spectra, while in a third combination, a SVRDM is utilized to analyze protein mass spectra and a BN is utilized to analyze micro array data, or vice versa.

Before describing a SVDRM, a support vector representation machine (SVRM) will be described. Consider two classes, where $C_1$ is the object class, and $C_0$ is the nonobject class. The task of one-class classification is to find the decision region $R_1$ for $C_1$ such that if an input $x \in R_1$, x is assigned to $C_1$; otherwise, it is rejected as $C_0$. Suppose there are N training vectors $\{x_1, \ldots, x_N\}$ from $C_1$, and no training vectors from $C_0$. The training task is to find an evaluation function $f_1(x)$, which gives the confidence of the input x being in the object class. The region $R_1$ is defined as $R_1=\{x: f_1(x) \geq T\}$ to contain those object samples x giving evaluation-function values above some threshold T. To achieve a high recognition rate, training vectors should produce high evaluation-function values.

A mapping from the input space to a high-dimensional feature space is defined as $\Phi: R \tau F$, where R is the input space and F is the transformed feature space. The explicit form of $\Phi$ and calculation of $\Phi(x)$ are not necessary. Rather, only the inner product $\Phi(x_i)^T \Phi(x_j)$ need be specified to be some kernel function. To evaluate $\Phi^T \Phi$, evaluate the associated kernel function. According to an embodiment of the invention, a Gaussian kernel $\exp(-|x_i-x_j|^2/2\sigma^2)$ is used, since it simplifies volume estimation and has other desirable properties. For a Gaussian kernel, the transformed training and test vectors lie on the unit sphere centered at the origin in F. Since the data are automatically normalized to be of unit length, the distance between two vectors in F can be represented by their inner product. Thus, as an evaluation function the inner product $f_1(x)=h^T\Phi(x)$ can be used, where h is a vector in F that we compute from the training set. It describes the SVRM and is used to determine the class of test inputs.

The solution h for the SVRM satisfies $\text{Min}|h|^2/2$ $h^T\Phi(x_i) \geq T=1, i=1, \ldots, N.$ The second condition above ensures large evaluation function values for the training set, greater than some threshold T, which is preferably equal to 1. The norm $|h|$ of h is minimized in the first condition to reduce the volume of $R_1$ to provide rejection of nonobjects. It can be shown that a solution h with a lower norm provides a smaller class-$C_1$ acceptance volume. Outliers (errors) are expected, however, and the second constraint above will not be satisfied for all of the training set. Thus, slack variables $\xi_i$ are introduced, and h satisfies $$\text{Min}\left\{\frac{|h|^2}{2} + C\sum_{i=1}^{N}\xi_i\right\},$$

$$h^T\Phi(x_i) \geq T = 1 - \xi_i, i = 1, \ldots, N,$$

$$\xi_i \geq 0, \qquad i = 1, \ldots, N,$$

This allows for classification errors by amounts $\xi_i$ for various training-set samples $x_i$. The factor C in the first condition is the weight of the penalty term for the slack variables. The solution h is a linear combination of the support vectors, which are a small portion of the entire training set. To classify an input x, form the inner product $h^T\Phi(x)$; if this is at or above some threshold T, classify x as a member of the object class. In many circumstances, the training set is not adequate to represent the test set. Thus, in practice, a threshold T<1 is used in the above equations, and a decision region that is larger than that occupied by only the training data is used.

A SVRDM classifier is a SVRM extended to the multiple object class case. Consider K object classes with $N_k$ training samples per class; the training vectors for class k are $\{x_{ki}\}$. To consider classification and rejection, define $P_C$ as the classification rate, which is the percentage of the object class samples that are classified in the correct object class, and define $P_R$ as the rejection rate, which is the rate of object-class samples rejected as the nonobject class. $P_E$ is defined as the classification error rate, which is the rate of object-class samples classified in the wrong object classes. Thus, $P_C+P_R+P_E=1$. $P_{FA}$ is the percentage of the nonobject-class samples mistakenly classified as being in an object class (i.e., false alarms). The objective is to obtain a high $P_C$ and a low $P_{FA}$. The classifier approach is to obtain K functions $h_k$; each discriminates one of the K classes $\{k\}$ from the other K-1 classes. For a given test input x, calculate the vector inner product (VIP) of $\Phi(x)$ with each $h_k$. If any of these kernel VIPs are $\mu T$, x is assigned to the class producing the maximum VIP value; otherwise it is rejected. It is assumed that there are no nonobject-class samples in the training set. For simplicity, consider first a two-object-class problem. For class 1 samples $x_{1i}$, the evaluation-function VIP output is $h_1^T\Phi(x_{1i}) \geq T$ and $h_2^T\Phi(x_{1i}) \leq p$. For class 2 samples $x_{2j}$, the output is $h_2^T\Phi(x_{2j}) \geq T$ and $h_1^T\Phi(x_{2j}) \leq p$. The parameter p is the maximum evaluation-function value that can be accepted for the other object-class samples. The two solution vectors $h_1$ and $h_2$ thus satisfy $\text{Min}|h_1|^2/2$ $h_1^T\Phi(x_{1i}) \geq 1 \ i=1, \ldots, N_1,$ $h_1^T\Phi(x_{2j}) \leq p \ j=1, \ldots, N_2,$ and $\text{Min}|h_2|^2/2$ $h_2^T\Phi(x_{2i}) \geq 1 \ i=1, \ldots, N_1,$ $h_2^T\Phi(x_{1j}) \leq p \ j=1, \ldots, N_2,$ Note that the VIP kernel-function value for the object class to be discriminated against is specified to be p in this case. The difference in the formulation of the SVRM and the SVRDM lies in the third condition above; this condition provides discrimination information between object classes by using p>–1 and p<–1 (the SVM solution is p=–1) and rejection of nonobjects. In the presence of outliers (training-class errors), slack variables $\xi_i$ are of course used in both $h_1$ and $h_2$. The final version for $h_1$ is thus $$\text{Min}\left\{\frac{|h_1|^2}{2} + C(\sum \xi_{1i} + \sum \xi_{2j})\right\},$$
$$h_1^T \Phi(x_{1i}) \geq 1 - \xi_{1i}, \quad i = 1, \ldots, N_1,$$
$$h_1^T \Phi(x_{2j}) \leq p + \xi_{2j}, \quad j = 1, \ldots, N_2,$$
$$\xi_{1i} \geq 0, \qquad \xi_{2j} \geq 0,$$

and $h_2$ is similar.

For a K-class problem, an SVRDM contains K functions $h_k$, similar to $h_1$ in the SVRM case. Each recognizes one of the K classes (training-set samples $x_{ki}$) with a vector inner product $\mu l$ and all other training-set samples in the other K–1 classes (training-set samples $x_{mj}$, where m≠k) with a vector inner product [p. For a test input x, if the maximum of the transformed vector inner products for all of the K functions $h_k$ is $\mu T$, the test sample is placed in that class that produces the maximum vector inner product; otherwise, it is rejected as a non-object.

A Bayesian network (BN) is a probabilistic graphical model in which the nodes represent random variables, and the edges represent conditional independence assumptions. In addition, a conditional probability distribution (CPD) is associated with each node. A BN is also a directed graph, in which the direction of an edge is indicative of a deterministic relationship between the nodes. Then, the CPD indicates the probability that a child node takes on each of its different values for each combination of parent nodes. Bayesian networks allow one to determine chains of probabilistic inference, including determining causation and explaining away.

According to an embodiment of the invention, an efficient algorithm for constructing Bayesian belief networks from databases takes a database and an attributes ordering (i.e., the causal attributes of an attribute should appear earlier in the order) as input and constructs a belief network structure as output. A belief network can be viewed as a network system of information channels, where each node is a valve that is either active or inactive and the valves are connected by noisy information channels (edges). The information flow can pass through an active valve but not an inactive one. When all the valves (nodes) on one undirected path between two nodes are active, this path is said to be open. If any one valve in the path is inactive, the path is said to be closed. When all paths between two nodes are closed given the status of a set of valves (nodes), the two nodes are said to be d-separated by the set of nodes. The status of valves can be changed through the instantiation of a set of nodes. The amount of information flow between two nodes can be measured by using mutual information, when no nodes are instantiated, or conditional mutual information, when some other nodes are instantiated.

In information theory, the mutual information of two nodes $X_i$, $X_j$, is defined as $$I(X_i, X_j) = \sum_{x_i, x_j} P(x_i, x_j) \log \frac{P(x_i, x_j)}{P(x_i)P(x_j)},$$

and conditional mutual information is defined as $$I(X_i, X_j | C) = \sum_{x_i, x_j, c} P(x_i, x_j, c) \log \frac{P(x_i, x_j | c)}{P(x_i | c)P(x_j | c)},$$

where $X_i$, $X_j$ are two nodes and C is a set of nodes. According to an embodiment of the invention, conditional mutual information is used as a conditional independence test to measure the average information between two nodes when the statuses of some valves are changed by the condition-set C. When $I(X_i, X_j|C)$ is smaller than a certain threshold value $\epsilon$, $X_i$, $X_j$ are said to be d-separated by the condition-set C, and they are conditionally independent. This algorithm also makes the following assumptions: (1) The database attributes have discrete values and there are no missing values in all the records; (2) The volume of data is large enough for reliable conditional independence tests; and (3) The ordering of the attributes is available before the network construction, i.e., a node's parents nodes should appear earlier in the order.

According to an embodiment of the invention, this algorithm has three phases: drafting, thickening and thinning. In the first phase, this algorithm computes mutual information of each pair of nodes as a measure of closeness, and creates a draft based on this information. In the second phase, the algorithm adds edges when the pairs of nodes cannot be d-separated. The result of the second phase is an independence map of the underlying dependency model. In the third phase, each edge of the independence map is examined using conditional independence tests and will be removed if the two nodes of the edge can be d-separated.

According to an embodiment of the invention, the drafting phase can be summarized as follows.

1. Initiate a graph G(V E) where V={all the nodes of a data set} and E={ }. Initiate two empty ordered sets S, R.

2. For each pair of nodes $(v_i, v_j)$ where $v_i, v_j \in V$, compute the mutual information $I(v_i, v_j)$. For those pairs of nodes that have mutual information greater than a certain small value $\epsilon$, sort them by their mutual information from large to small and put them into an ordered set S.

3. Remove the first two pairs of nodes from S. Add the corresponding edges to E (the direction of the edges in this algorithm is determined by the previously available node ordering).

4. Remove the first remaining pair of nodes from S. If there is no open path between the two nodes (these two nodes are d-separated given empty set), add the corresponding edge to E; otherwise, add the pair of nodes to the end of an ordered set R.

5. Repeat step 4 until S is empty.

Figure 4A:
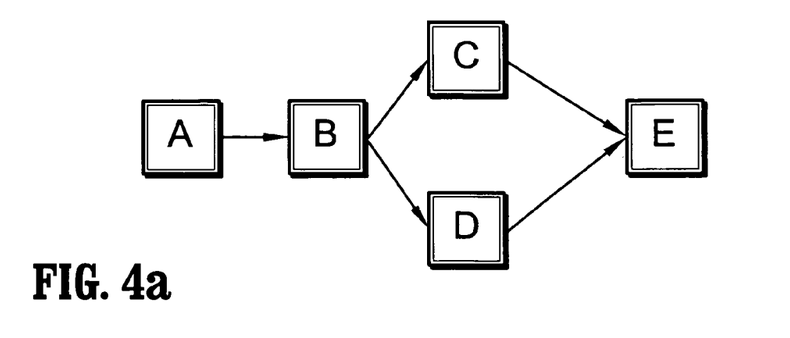
FIG. 4 depicts a simple multi-connected network, according to an embodiment of the invention.

For the purpose of illustrating this algorithm's working mechanism, consider a database that has underlying Bayesian network illustrated in FIG. 4a; and also order the nodes as A, B, C, D, E. After step 2, one can get the mutual information of all 10 pair of nodes. Suppose I(B,D)μI(C,E)

Figure 4B:
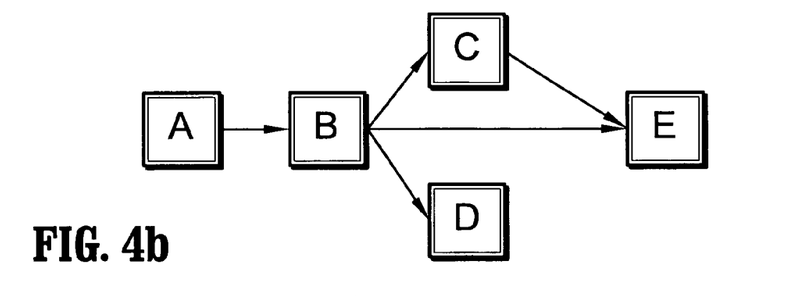

$\mu I(B,E)\mu I(A,B)\mu I(B,C)\mu I(C,D)\mu I(D,E)\mu I(A,D)\mu I(A,E)\mu I(A,C)$, and all the mutual information is greater than $\epsilon$, one can construct a draft graph as shown in FIG. 4b after step 5. Note that the order of mutual information between nodes is not arbitrary. For example, from information theory, $I(A,C) < Min(I(A,B),I(B,C))$. When the underlying graph is sparse, Phase I can construct a graph very close to the original one. If the underlying graph is a singly connected graph (a graph without an undirected cycle), Phase I guarantees the constructed network is the same as the original one. In this example, (B,E) is wrongly added and (D,E) is missing because of the existing open path (D-B-E) and (D-B-C-E). The draft graph created in this phase is the base for next phase.

According to an embodiment of the invention, the thickening phase can be summarized as follows.

6. Remove the first pair of nodes from R.

7. Find a block set that blocks each open path between these two nodes by a set of minimum number of nodes. Conduct a conditional independence test. If these two nodes are still dependent on each other given the block set, connect them by an edge.

8. go to step 6 until R is empty.

Figure 4C:
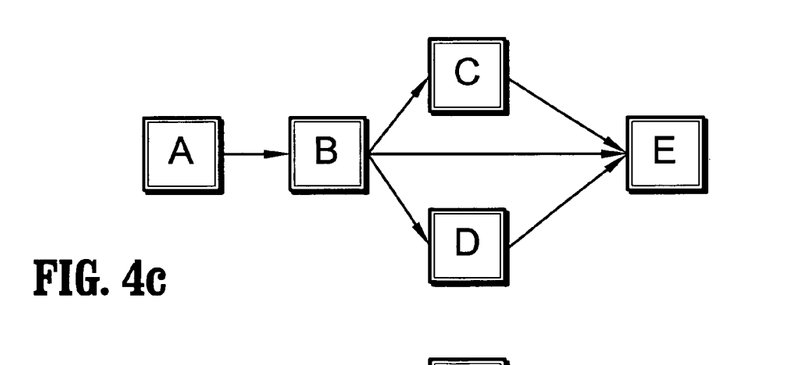

The graph after Phase II is shown in FIG. 4c. When this algorithm examines the pair of nodes (D,E) in step 7, it finds that {B} is the minimum set which blocks all the open paths between D and E. Since the conditional independence test can reveal that D and E are still dependent given {B}, edge (D,E) is added. Edge (A,C) is not added because the conditional independence test reveals that A and C are independent given block set {B}. Edge (A,D), (C,D) and (A,E) are not added for the same reason. In this phase, the algorithm examines all pairs of nodes that have mutual information greater than $\epsilon$, an edge is not added when the two nodes are independent given some block set. It is possible that some edges are wrongly added in this phase.

According to an embodiment of the invention, the thinning phase can be summarized as follows.

Figure 4D:
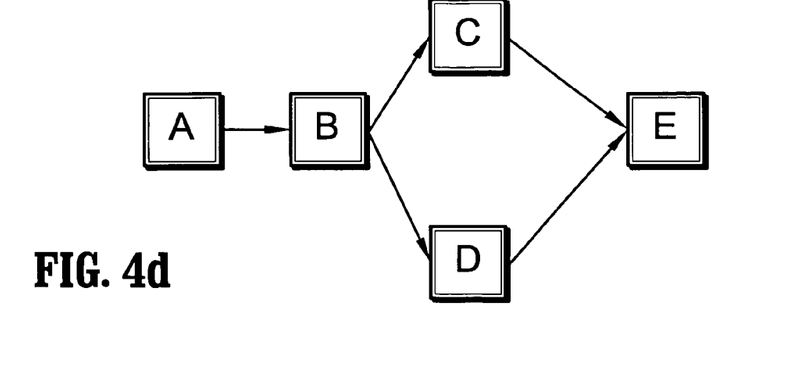

9. For each edge in E, if there are open paths between the two nodes besides this edge, remove this edge from E temporarily and find a block set that blocks each open path between these two nodes by a set of minimum number of nodes. Conduct a conditional independence test on the condition of the block set. If the two nodes are dependent, add this edge back to E; otherwise remove the edge permanently. The 'thinned' graph is shown in FIG. 4d, which is the same as the original graph. Edge (B,E) is removed because B and E are independent given {C,D}.

According to an embodiment of the invention, an algorithm for finding a block set that blocks each open path between these two nodes by a set of minimum number of nodes is as follows. Because this procedure uses a greedy search method, it does not guarantee that a minimum block set is found.

Procedure find_block_set (current graph, node1, node2)
begin
find all the undirected paths between node1 and node2;
store the open paths in open_path_set, store the closed paths in closed_path_set;
do
   while there are open paths which have only one node do
     store the nodes of each such path in the block set;
     remove all the blocked paths by these nodes from the open_path_set and closed_path_set;
     from the closed_path_set, find paths opened by the nodes in block set and move them to the open_path_set, shorten such paths by removing the nodes that are also in the block set;
   end while
   if there are open paths do
     find a node which can block maximum number of the rest paths and put it in the block set;
     remove all the blocked paths by the node from the open_path_set and the closed_path_set;
     from the closed_path_set, find paths opened by this node and move them to the open_path_set, shorten such paths by removing the nodes that are also in the block set;
   end if
until there are no open path
end procedure.

Figure 1:
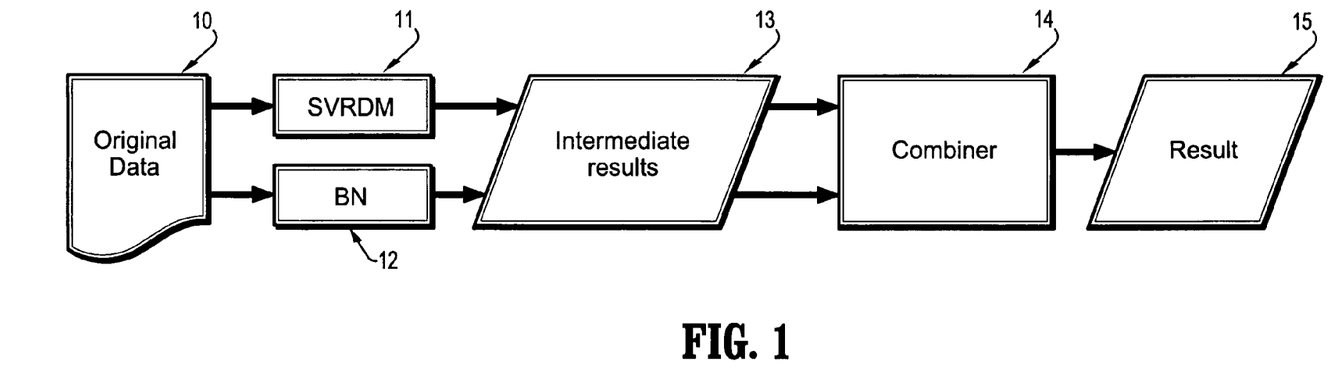
FIG. 1 depicts a schematic diagram of the combination of the two classifiers according to an embodiment of the invention.

According to an embodiment of the invention, a schematic diagram of the combination of the two classifiers, a support vector representation and discrimination machines (SVRDM) and a Bayesian network (BN), is illustrated in FIG. 1. Biological data 10 is input to both classifiers 11, 12, in parallel. A combiner 14 uses the intermediate results 13 of both classifiers at the same time. The result 15 is a merged decision, which is itself a classification. Combining classifiers allows one to combine classifiers trained on different feature sets, different training sets, different classification methods, or different training sessions, to improve overall classification accuracy.

Figure 2:
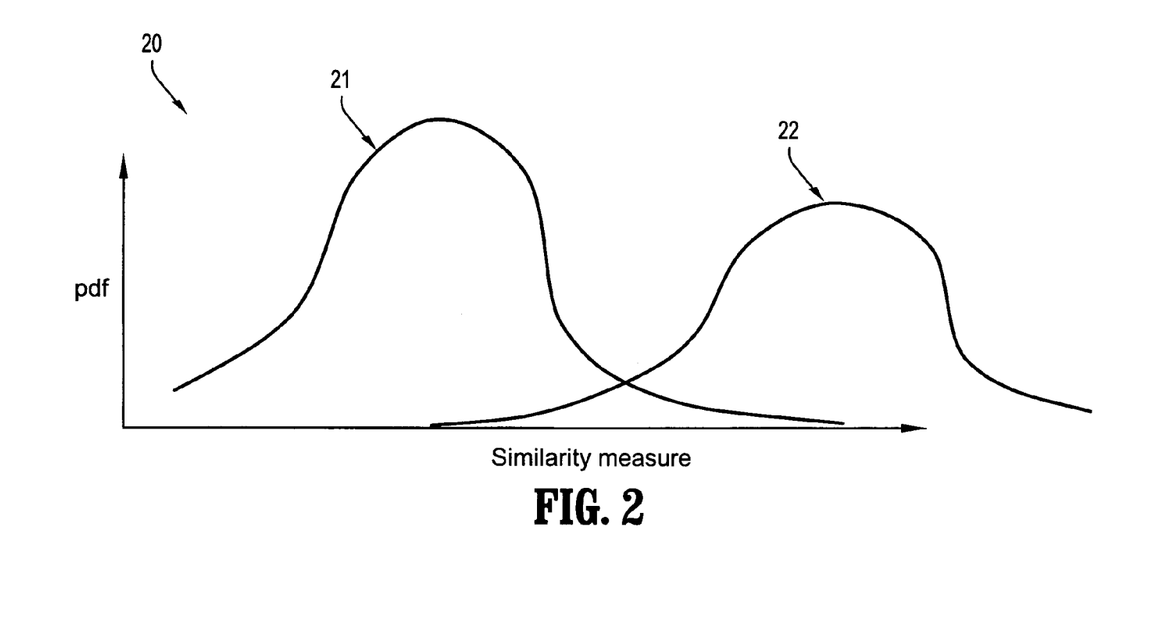
FIG. 2 illustrates the decision uncertainty for two exemplary probability distribution functions according to an embodiment of the invention.

A single classifier usually has a particular uncertainty in its decision, which can be described by a probability density function for each class. FIG. 2 illustrates the decision uncertainty for two exemplary probability distribution functions (PDFs). The graph 20 shows the PDFs plotted as a function of similarity measure. The PDFs of a classifier for two different classes are illustrated and are assumed to have a bell shape. A PDF for class A is represented by curve 21, while a PDF for class B is represented by curve 22. As can be seen from the figure, the two bell curves may overlap, and the area of the overlap is a measure of the quality of the classification algorithm. Classification results which are between the two bell curves would have high uncertainty, whereas classification results far away from the middle would have a low uncertainty.

Figure 3:
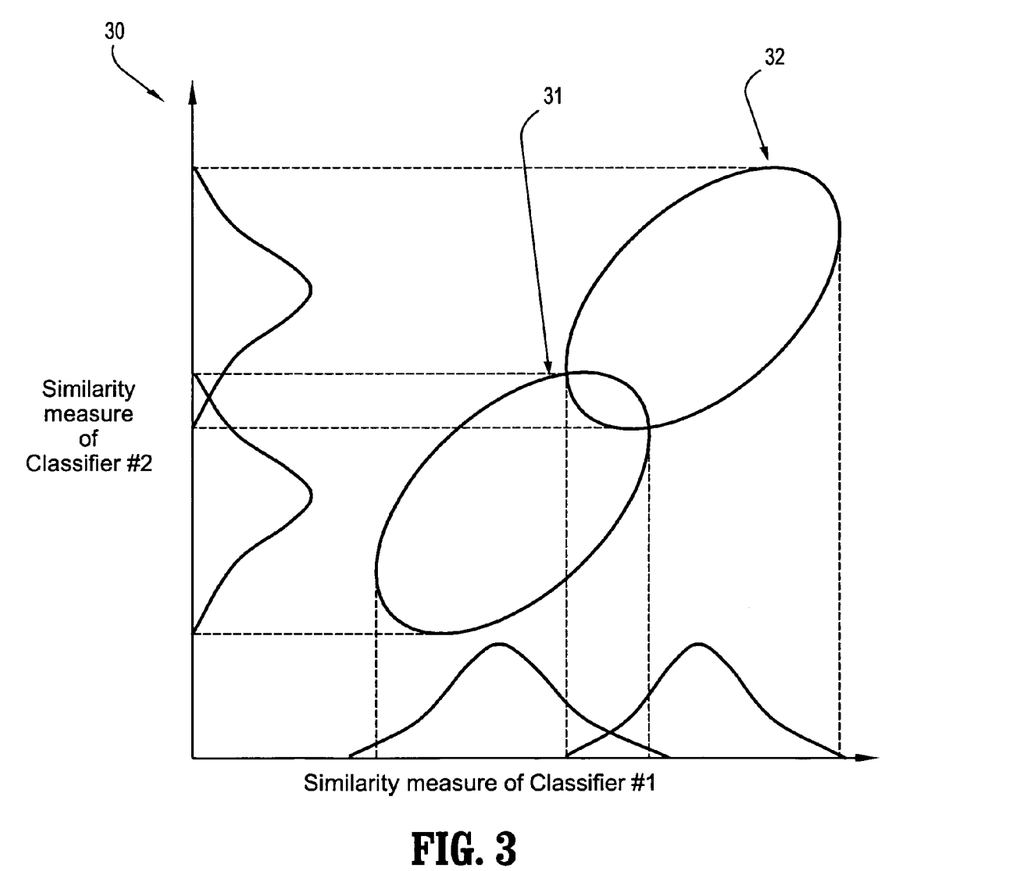
FIG. 3 illustrates a combination of two classifier distributions for two different classes according to an embodiment of the invention.

According to an embodiment of the invention, a classifier uses a combination of two classifiers that are not strongly correlated to each other, where if a given instance is classified by one classifier with a high uncertainty, the other can give a classification with a low uncertainty, and vice versa. In that situation, a combined decision can be generated with a lower uncertainty. FIG. 3 illustrates a combination of two classifier distributions for two different classes. The graph 30 has the similarity measure of the first classifier plotted along the horizontal axis, while the similarity measure of the second classifier plotted along the vertical axis, with the shapes of the corresponding PDFs sketched along the corresponding axis. The regions of the similarity space where the corresponding PDFs are at a maximum are indicated by the ellipses 31, 32. Ellipse 31 indicates the region where the PDF for class A is at a maximum, while ellipse 32 indicates the region where the PDF for class B is at a maximum. The raw data can be identical for both classifiers or the data can differ but describe the same classes.

By combining the intermediate results of both classifiers, even if there is a large overlap in the class PDFs for each classifier individually, the area of overlap of the combined PDFs should decrease in order to provide improved classification performance. Note that, in accordance with an embodiment of the invention, the combiner is a classifier itself, which has as input the classification results of the BN and SVRDM with their uncertainties. The combiner then divides the decision areas in two parts, which correspond with the two different classes.

The type of classifier incorporated in the combiner depends on the distribution of the feature vector data as well as on the distribution of the classification results of BN and SVRDM. Some combiners are adaptive in that the combiner weighs the decisions of individual classifiers depending on the input patterns. Adaptive combination schemes can also exploit the detailed error characteristics and expertise of the individual classifiers. In addition, different combiners expect different types of output from the individual classifiers. These expectations can be categorized into three groups: (1) measurement (or confidence); (2) rank; and (3) abstract. At the confidence level, the individual classifier outputs a numerical value for each class indicating the probability that the given input pattern belongs to that class. At the rank level, the classifier assigns a rank to each class with the highest rank being the first choice. At the abstract level, a classifier only outputs a unique class label (or several class labels where the classes are equally probable). The confidence level imparts the most information, while the abstract level imparts the least information about the decision being made.

The SVRDM has been applied to a ship and face databases and has been proven superior to the SVM in terms of rejection and classification. The empirical results on a set of standard benchmark datasets show that Bayesian networks are excellent classifiers.

Combination classifiers in accordance with an embodiment of the invention have application for the combined analysis of protein and gene expression data for healthy persons and patients of certain illnesses, such as lung cancer. Models for each data set and for each classifier can be built and the combination will then give a combined model, which allows a mapping of genotype information to the phenotype information.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 5:
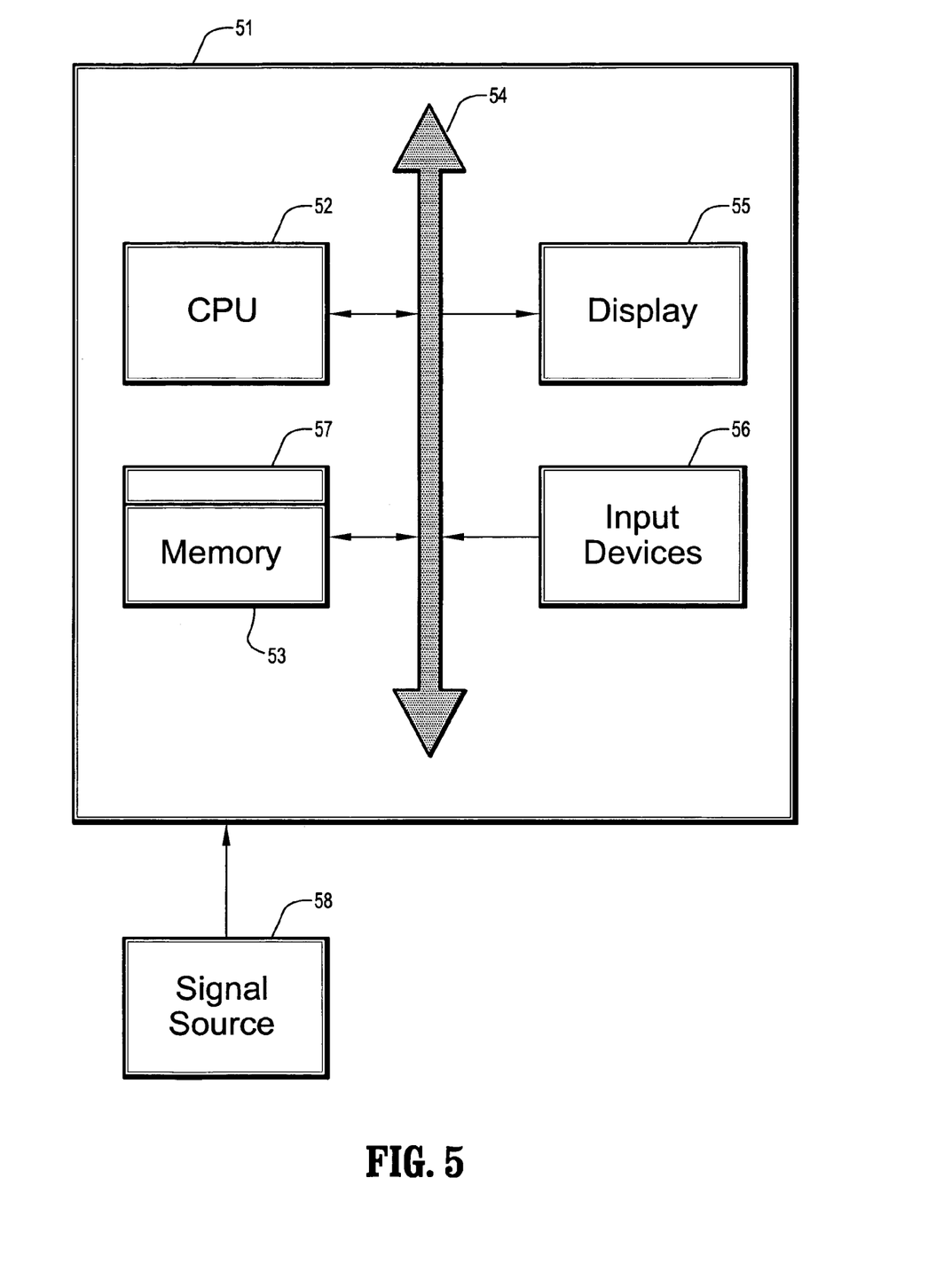
FIG. 5 is a block diagram of an exemplary computer system for implementing a combined BN and SVM according to an embodiment of the invention.

FIG. 5 is a block diagram of an exemplary computer system for implementing a combined BN and SVM according to an embodiment of the invention. Referring now to FIG. 5, a computer system 51 for implementing the present invention can comprise, inter alia, a central processing unit (CPU) 52, a memory 53 and an input/output (I/O) interface 54. The computer system 51 is generally coupled through the I/O interface 54 to a display 55 and various input devices 56 such as a mouse and a keyboard. The support circuits can include circuits such as cache, power supplies, clock circuits, and a communication bus. The memory 53 can include random access memory (RAM), read only memory (ROM), disk drive, tape drive, etc., or a combinations thereof. The present invention can be implemented as a routine 57 that is stored in memory 53 and executed by the CPU 52 to process the signal from the signal source 58. As such, the computer system 51 is a general purpose computer system that becomes a specific purpose computer system when executing the routine 57 of the present invention.

The computer system 51 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for analyzing biological microarray data and protein mass spectra data comprising the steps of:
classifying said microarray data in a first classifier;
classifying said protein mass spectra data in a second classifier;
combining the results of the first classifier with the results of the second classifier; and
analyzing the results as a function of the similarity measure of the first classifier and the similarity measure of the second classifier.

2. The method of claim 1, wherein the first set of biological data and the second set of biological data are the same.

3. The method of claim 1, wherein the first classifier is a support vector representation and discrimination machine.

4. The method of claim 1, wherein the second classifier is a Bayesian network.

5. The method of claim 4, wherein said Bayesian network comprises computing mutual information of pairs of data of said data set, creating a draft network based on the mutual information, wherein data item of said data set comprise nodes of said network and the edges connecting a pair of data nodes represent the mutual information of said nodes, thickening said network by adding edges when pairs of data nodes cannot be d-separated, and thinning said network by analyzing each edge of said draft network with a conditional independent test and removing said edge if said corresponding data nodes can be d-separated.

6. The method of claim 1, wherein the results of the first classifier and the second classifier are combined in parallel.

7. The method of claim 1, wherein said combining step comprises weighing the results of the first and second classifiers based on the input patterns.

8. A program storage device readable by a computer, tangibly embodying a program of instructions executable by the computer to perform the method steps for analyzing biological microarray data and protein mass spectra data, said method comprising the steps of:

classifying said microarray data in a first classifier;

classifying said protein mass spectra data in a second classifier;

combining the results of the first classifier with the results of the second classifier, and analyzing the results as a function of the similarity measure of the first classifier and the similarity measure of the second classifier.

9. The computer readable program storage device of claim 8, wherein the first set of biological data and the second set of biological data are the same.

10. The computer readable program storage device of claim 8, wherein the first classifier is a support vector representation and discrimination machine.

11. The computer readable program storage device of claim 8, wherein the second classifier is a Bayesian network.

12. The computer readable program storage device of claim 11, wherein said Bayesian network comprises computing mutual information of pairs of data of said data set, creating a draft network based on the mutual information, wherein data item of said data set comprise nodes of said network and the edges connecting a pair of data nodes represent the mutual information of said nodes, thickening said network by adding edges when pairs of data nodes cannot be d-separated, and thinning said network by analyzing each edge of said draft network with a conditional independent test and removing said edge if said corresponding data nodes can be d-separated.

13. The computer readable program storage device of claim 8, wherein the results of the first classifier and the second classifier are combined in parallel.

14. The computer readable program storage device of claim 8, wherein said combining step comprises weighing the results of the first and second classifiers based on the input patterns.

15. A method for analyzing biological data comprising the steps of:

classifying a set of microarray data in a first classifier, wherein said first classifier is a support vector representation and discrimination machine, wherein said machine discriminates said data into a plurality of classes using a plurality of discrimination functions, wherein an inner product of each said discrimination function with a kernel function is evaluated on said data, wherein the norm of each said discrimination is minimized, and wherein the value of each said inner product is compared to a threshold to determine whether a microarray data item belongs to a class associated with said discrimination function;

classifying a set of protein mass spectra data in a second classifier, wherein said second classifier is a Bayesian network; and analyzing the combined results of said first classifier and said second classifier as a function of the similarity measure of the first classifier and the similarity measure of the second classifier.

* * * * *